US012693226B2

(12) United States Patent
Hong et al.

(10) Patent No.: US 12,693,226 B2
(45) Date of Patent: Jul. 28, 2026

(54) APPARATUS AND METHOD FOR MEASURING CHLORINE IONS IN CONCRETE

(71) Applicant: Shenzhen University, Shenzhen City (CN)

(72) Inventors: Shuxian Hong, Shenzhen City (CN); Biqin Dong, Shenzhen City (CN); Xu Wang, Shenzhen City (CN)

(73) Assignee: Shenzhen University, Shenzhen City (CN)

( * ) Notice: Subject to any disclaimer, the term of this patent is extended or adjusted under 35 U.S.C. 154(b) by 52 days.

(21) Appl. No.: 19/028,115

(22) Filed: Jan. 17, 2025

(65) Prior Publication Data

US 2025/0389666 A1    Dec. 25, 2025

(30) Foreign Application Priority Data

Jun. 19, 2024    (CN) .......................... 202410797144.8

(51) Int. Cl.
*G01N 21/71*          (2006.01)
*G01N 33/38*          (2006.01)

(52) U.S. Cl.
CPC ......... *G01N 21/718* (2013.01); *G01N 33/383* (2013.01); *G01N 2201/06113* (2013.01); *G01N 2201/0694* (2013.01); *G01N 2201/0697* (2013.01)

(58) Field of Classification Search
CPC ............... G01N 21/718; G01N 33/383; G01N 2201/06113; G01N 2201/0694; G01N 2201/0697
See application file for complete search history.

(56) References Cited

U.S. PATENT DOCUMENTS

2012/0029836 A1*   2/2012   Hermann ................ G01J 3/443
                                                                702/28

OTHER PUBLICATIONS

Jian Huang, Jingqi Lu, Huan Yang, Xiangdong Cao. Quantitative Analysis on Coal Calorific Value Using Nanosecond, Femtosecond, and Dual-Pulse Laser-Induced Breakdown Spectroscopy[J]. Laser & Optoelectronics Progress, 2019, 56(19):193002 (Year: 2019).*

(Continued)

*Primary Examiner* — Kara E. Geisel
*Assistant Examiner* — Paul Schnase
(74) *Attorney, Agent, or Firm* — Shu Chen

(57)          ABSTRACT

This application provides an apparatus and a method for measuring chlorine ions in concrete, and relates to the technical field of chlorine ion measurement. The apparatus includes a first optical path system, a second optical path system, a spectrometer, and a central control unit, where the first optical path system includes a femtosecond laser device, an ablative focusing lens group, and a sample; and the second optical path system includes a heating light source, a dichroic mirror, a reflecting mirror, and a heating laser focusing lens group. According to this application, the femtosecond laser device is used as an ablative light source, improving sample ablation efficiency and resolving a problem that a chlorine ion spectral line is weak. In addition, a clustering algorithm is adopted in a sampling process in this application, resolving problems such as a large quantitative error and poor repeatability caused by non-heterogeneity of the concrete.

7 Claims, 5 Drawing Sheets

(56) References Cited

OTHER PUBLICATIONS

Gaudiuso R, Dell'Aglio M, De Pascale O, Senesi GS, De Giacomo A. Laser induced breakdown spectroscopy for elemental analysis in environmental, cultural heritage and space applications: a review of methods and results. Sensors (Basel). 2010;10(8):7434-68. (Year: 2010).*

Machine translation of Huang into English (Year: 2019).*

Huang Jian; Lu Jingqi; Yang Huan; Cao Xiangdong, "Quantitative Analysis on Coal Calorific Value Using Nanosecond, Femtosecond, and Dual-Pulse Laser-Induced Breakdown Spectroscopy," Laser & Optoelectronics Progress, vol. 56, Issue 19, pp. 193002-1 to 193002-8 (Oct. 2019); China Academic Journal Electronic Publishing House.

First Office Action issued in Chinese application No. CN202410797144.8 by the State Intellectual Property Office of People's Republic of China on Jan. 5, 2025; 4 pages.

English translation of First Office Action issued in Chinese application No. CN202410797144.8 by the State Intellectual Property Office of People's Republic of China on Jan. 5, 2025; 6 pages.

Second Office Action issued in Chinese application No. CN202410797144.8 by the State Intellectual Property Office of People's Republic of China on Apr. 9, 2025; 5 pages.

English translation of Second Office Action issued in Chinese application No. CN202410797144.8 by the State Intellectual Property Office of People's Republic of China on Apr. 9, 2025; 7 pages.

Rejection Decision issued in Chinese application No. CN202410797144.8 by the State Intellectual Property Office of People's Republic of China on Jun. 9, 2025; 4 pages.

English translation of Rejection Decision issued in Chinese application No. CN202410797144.8 by the State Intellectual Property Office of People's Republic of China on Jun. 9, 2025; 4 pages.

Reconsideration Decision issued in Chinese application No. CN202410797144.8 by the State Intellectual Property Office of People's Republic of China on Aug. 29, 2025; 1 page.

English translation of Reconsideration Decision issued in Chinese application No. CN202410797144.8 by the State Intellectual Property Office of People's Republic of China on Aug. 29, 2025; 1 page.

* cited by examiner

APPARATUS AND METHOD FOR MEASURING CHLORINE IONS IN CONCRETE

CROSS REFERENCE TO RELATED APPLICATION

This patent application claims the benefit and priority of Chinese Patent Application No. 2024107971448, filed with the China National Intellectual Property Administration on Jun. 19, 2024, the disclosure of which is incorporated by reference herein in its entirety as part of the present application.

TECHNICAL FIELD

The present disclosure relates to the technical field of chlorine ion measurement, and in particular, relates to an apparatus and a method for measuring chlorine ions in concrete.

BACKGROUND

Reinforced concrete is one of the most widely used materials in buildings. However, reinforcing steel bars inside the reinforced concrete may be rusted due to invasion of chloride ions. As a result, structural safety and material durability rapidly deteriorate. Therefore, the current standards pose strict requirements on the chloride ions content in concrete. For example, the content of chloride ions in sand of prestressed concrete is limited to 0.01%, and content of water-soluble chloride ions in a colloid is limited to 0.06%, etc.

Therefore, in production and construction process of raw materials, it is necessary to measure the content of chlorine ions to ensure durability of a building. Traditional methods for detecting chloride ions are mainly based on potentiometric titration and X-ray fluorescence spectroscopy (XRF). In the potentiometric titration method, based on reaction between chloride ions and silver ions, a solubility of the chloride ions in a to-be-tested solution can be calculated according to a concentration of a titrant and a volume of a titrant consumed in a titration process. In the X-ray fluorescence spectroscopy, a solubility of chloride ions in a sample is determined by comparing intensity of fluorescence radiation of a sample with intensity of fluorescence radiation of a standard sample with a known solubility.

The following are disadvantages and reasons thereof of the traditional technology.

Based on a detection principle, problems in the two methods are mainly as follows:

(1) A complex sample preparation process is required, and different processing methods are required for different samples, making an operation inconvenient.

(2) It takes a long time, and several hours may be needed in one titration measurement. Some types of concrete may even need to be processed for more than 24 hours.

(3) In-situ measurement cannot be performed, measurement can only be performed in a laboratory, and a measurement result cannot be provided in a construction scenario.

(4) Only one type of particles can be detected at a time. During acceptance, particles specified in other standards such as sulfate ions should be sampled and measured for a plurality of times.

A current commonly-used method for detecting chloride ions is laser-induced breakdown spectroscopy (LIBS) that can achieve rapid, quantitative, and non-contact measurement of the chloride ions. The method has the advantages that: Sample processing is not required, a detection process is extremely quick, a detection condition is friendly, on-site online measurement can be achieved, and all elements can be measured simultaneously.

However, the following are disadvantages and reasons thereof of the LIBS detection method.

The LIBS detection method has a problem that a quantification limit for chloride ions is not high, which is caused by two reasons: Spectral line intensity of the chloride ions is weak, and it is difficult to meet detection limit requirements of the current standards. In addition, concrete has strong heterogeneity, with many pores inside, and a difference in absorption efficiency of components inside the concrete for laser energy results in poor repeatability of a detection result.

Therefore, how to design an apparatus and a method for measuring chloride ions in concrete that can resolve the problems such as weak chloride ion spectral lines, large quantitative errors caused by the heterogeneity of the concrete, and poor repeatability has become a technical problem to be urgently resolved in this field.

SUMMARY

An objective of the present disclosure is to provide an apparatus and a method for measuring chlorine ions in concrete. According to the present disclosure, a femtosecond laser device is used as an ablative light source, improving sample ablation efficiency and resolving a problem that a chlorine ion spectral line is weak. In addition, a clustering algorithm is adopted in a sampling process in the present disclosure, resolving problems such as a large quantitative error and poor repeatability caused by non-heterogeneity of the concrete.

To achieve the foregoing objective, the present disclosure provides the following technical solutions.

According to a first aspect, the present disclosure provides an apparatus for measuring chlorine ions in concrete. The apparatus includes a first optical path system, a second optical path system, a spectrometer, and a central control unit.

The first optical path system includes:

a femtosecond laser device, configured to emit ablative femtosecond laser;

an ablative focusing lens group, configured to focus the ablative femtosecond laser to obtain focused ablative femtosecond laser; and a sample, configured to receive the focused ablative femtosecond laser to generate a plasma.

The second optical path system includes:

a heating light source, configured to emit heating laser;| a dichroic mirror, configured to transmit the heating laser to obtain transmitted heating laser;

a reflecting mirror, configured to reflect the transmitted heating laser to obtain reflected heating laser; and a heating laser focusing lens group, configured to: focus the reflected heating laser to obtain focused heating laser, and irradiate the focused heating laser on the plasma to obtain a plasma with enhanced spontaneous emission strength.

The heating laser focusing lens group is further configured to focus spontaneous emission of the plasma with enhanced spontaneous emission strength to obtain focused plasma spontaneous emission.

The reflecting mirror is further configured to reflect the focused plasma spontaneous emission to obtain reflected plasma spontaneous emission.

The dichroic mirror is further configured to reflect the reflected plasma spontaneous emission for a second time to obtain plasma spontaneous emission that is reflected for a second time.

The spectrometer is configured to receive the plasma spontaneous emission that is reflected for a second time to obtain spectral information.

The central control unit is configured to perform clustering analysis on the spectral information to obtain content of the chlorine ions.

Optionally, the apparatus may further include:

a delay controller that is separately connected to the femtosecond laser device, the heating light source, and the spectrometer, and is configured to: provide system time and separately control operation of the femtosecond laser device, the heating light source, and the spectrometer.

Optionally, the first optical path system and the second optical path system are configured to perform excitation in a manner in which double beams are obliquely incident at an angle of 45°.

Optionally, the heating light source is wavelength-adjustable nanosecond laser.

According to a second aspect, the present disclosure provides a method for measuring chlorine ions in concrete based on the apparatus for measuring chlorine ions in concrete in the first aspect. The method includes:

irradiating ablative femtosecond laser on a sample to obtain a plasma;

irradiating heating laser on the plasma to obtain a plasma with enhanced spontaneous emission strength;

obtaining spectral information according to spontaneous emission of the plasma with enhanced spontaneous emission strength; and performing clustering analysis on the spectral information to obtain content of the chlorine ions.

Optionally, the irradiating ablative femtosecond laser on a sample to obtain a plasma specifically includes:

focusing, by an ablative focusing lens group, the ablative femtosecond laser emitted by a femtosecond laser device to obtain focused ablative femtosecond laser; and vertically irradiating the focused ablative femtosecond laser on a sample, to obtain a plasma Optionally, the irradiating heating laser on the plasma to obtain a plasma with enhanced spontaneous emission strength specifically includes:

transmitting, by a dichroic mirror, the heating laser emitted by a heating light source to obtain transmitted heating laser;

reflecting, by a reflecting mirror, the transmitted heating laser to obtain reflected heating laser;

focusing, by a heating laser focusing lens group, the reflected heating laser to obtain focused heating laser; and irradiating the focused heating laser on the plasma at an incident angle of 45°, to obtain the plasma with enhanced spontaneous emission strength.

Optionally, the obtaining spectral information according to spontaneous emission of the plasma with enhanced spontaneous emission strength specifically includes:

focusing, by a heating laser focusing lens group, spontaneous emission of the plasma with enhanced spontaneous emission strength to obtain focused plasma spontaneous emission;

reflecting, by a reflecting mirror, the focused plasma spontaneous emission to obtain reflected plasma spontaneous emission;

reflecting, by a dichroic mirror, the reflected plasma spontaneous emission for a second time to obtain plasma spontaneous emission that is reflected for a second time; and receiving, by a spectrometer, the plasma spontaneous emission that is reflected for a second time to obtain the spectral information.

Optionally, the performing clustering analysis on the spectral information to obtain chlorine ion specifically includes:

performing the clustering analysis on the spectral information to obtain a spectral intensity of the chlorine ions; and determining the content of the chlorine ions according to a relational expression between the spectral intensity of chlorine ions and the content of chlorine ions.

Optionally, the relational expression between the spectral intensity of chlorine ions and the content of chlorine ions is as follows:

$$I = FC_s A \frac{g_k e^{\frac{-E_k}{k_B T}}}{U(T)},$$

where

I is the spectral intensity of the chlorine ions, F is a system constant, $C_s$ is the content of the chlorine ions, A is a transition probability at a corresponding energy level, $g_k$ is energy level degeneracy, $E_k$ is energy at an energy level, $k_B$ is a Boltzmann constant, T is a plasma temperature, and U(T) is a partition function of the chlorine ions at the plasma temperature.

According to specific embodiments provided in the present disclosure, the present disclosure discloses the following technical effects:

According to the apparatus and the method for measuring chlorine ions in concrete provided in the present disclosure, in the present disclosure, the femtosecond laser device is used as an ablative light source to ablate the sample, such that the plasma is formed within short time. This can improve utilization efficiency of laser energy, can improve ablation efficiency, and can increase a signal-to-noise ratio of chloride ion radiation. In addition, the heating light source is used to irradiate the plasma, such that a temperature of the plasma increases. A higher temperature of the plasma indicates stronger radiation strength. In addition, the clustering algorithm is adopted in the sampling process, resolving problems such as a large quantitative error and poor repeatability caused by non-heterogeneity of the concrete.

BRIEF DESCRIPTION OF THE DRAWINGS

To describe the technical solutions in embodiments of the present disclosure or in the prior art more clearly, the accompanying drawings required for the embodiments are briefly described below. Apparently, the accompanying drawings in the following description show merely some embodiments of the present disclosure, and those of ordinary skill in the art may still derive other accompanying drawings from these accompanying drawings without creative efforts.

DETAILED DESCRIPTION OF THE EMBODIMENTS

The technical solutions of the embodiments of the present disclosure are clearly and completely described below with reference to the drawings in the embodiments of the present disclosure. Apparently, the described embodiments are merely a part rather than all of the embodiments of the present disclosure. All other examples obtained by a person of ordinary skill in the art based on the examples of the present disclosure without creative efforts shall fall within the protection scope of the present disclosure.

A laser-induced breakdown spectroscopy (LIBS) is a spectroscopic method, and is used to detect spontaneous radiation of a plasma. A LIBS system is configured to first focus laser on a surface of a sample through a convergent optical path, making the sample absorb energy to form an energy absorption area with extremely high energy density in a local area. Due to absorption of energy by atoms, the atoms are rapidly evaporated in a short period of time to form vapor. The sample vapor continues to absorb thermal energy or laser energy, ultimately leading to breakdown, in other words, electrons in the atoms absorb energy and escape, and the atoms are ionized to form plasmas. A measurement principle of LIBS is as follows: When the plasma starts to be cooled, energy is radiated outward in a form of an electromagnetic wave. In an early stage, the energy is radiated in a form of a high-intensity background spectrum of composite radiation and bremsstrahlung radiation. However, as a temperature of the plasma continues to decrease, energy level transition of elections starts to dominate, and a spectral signal is in a form of a discrete ionic spectral line, an atomic spectral line, and a molecular spectral band. Components and content thereof in the sample can be determined by receiving and analyzing the signal via the spectrometer.

An objective of the present disclosure is to provide an apparatus and a method for measuring chloride ions in concrete that can resolve the problems such as weak chloride ion spectral lines, large quantitative errors caused by the heterogeneity of the concrete, and poor repeatability.

In order to make the above objective, features and advantages of the present disclosure clearer and more comprehensible, the present disclosure will be further described in detail below in combination with accompanying drawings and particular implementation modes.

Embodiment 1

Figure 1:
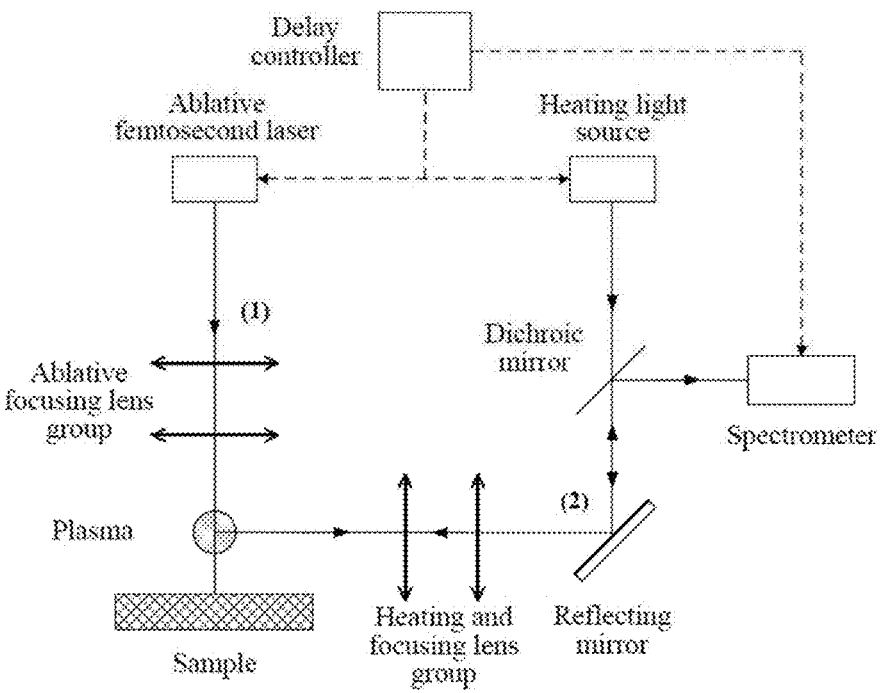
FIG. 1 is a schematic diagram of a structure of an apparatus for measuring chlorine ions in concrete according to Embodiment 1 of the present disclosure.

As shown in FIG. 1, this embodiment provides an apparatus for measuring chlorine ions in concrete. The apparatus is of a cross common-path optical path structure, and includes a first optical path system, a second optical path system, a spectrometer, and a central control unit.

The first optical path system includes a femtosecond laser device, an ablative focusing lens group, and a sample.

The femtosecond laser device is configured to emit ablative femtosecond laser.

The ablative focusing lens group is configured to focus the ablative femtosecond laser to obtain focused ablative femtosecond laser.

The sample is configured to receive the focused ablative femtosecond laser to generate a plasma.

The second optical path system includes a heating light source, a dichroic mirror, a reflecting mirror, and a heating laser focusing lens group.

The heating light source is configured to emit heating laser.|

The dichroic mirror is configured to transmit the heating laser to obtain transmitted heating laser.

The reflecting mirror is configured to reflect the transmitted heating laser to obtain reflected heating laser.

The heating laser focusing lens group is configured to: focus the reflected heating laser to obtain focused heating laser, and irradiate the focused heating laser on the plasma to obtain a plasma with enhanced spontaneous emission strength.

The heating laser focusing lens group is further configured to focus spontaneous emission of the plasma with enhanced spontaneous emission strength to obtain focused plasma spontaneous emission.

The reflecting mirror is further configured to reflect the focused plasma spontaneous emission to obtain reflected plasma spontaneous emission.

The dichroic mirror is further configured to reflect the reflected plasma spontaneous emission for a second time to obtain plasma spontaneous emission that is reflected for a second time.

The spectrometer is configured to receive the plasma spontaneous emission that is reflected for a second time to obtain spectral information.

The central control unit is configured to perform clustering analysis on the spectral information to obtain content of the chlorine ions.

It should be noted that, the femtosecond laser device is configured to focus the emitted femtosecond laser pulse on the surface of the sample to form the plasma. The heating light source is configured to enhance spontaneous emission strength of the plasma. The dichroic mirror not only can be configured to ensure transmission of a light beam of the heating light source, but also can be configured to ensure reflection of spontaneous emission of the plasma. The ablative focusing lens group and the heating laser focusing lens group are configured to focus a light beam. The central control unit is not shown in FIG. 1. For details, refer to FIG. 4. A specific process is as follows.

Ablative femtosecond laser and heating laser are separately incident at a large angle. The ablative femtosecond laser is vertically irradiated on the sample after passing through the ablative focusing lens group. The laser can be well ensured to be focused on the surface of the sample through the ablative focusing lens group, such that the sample is gasified in a short time. After a specific time interval, heating laser is irradiated on the plasma at a specific wavelength to be excited, such that a quantity of energy level electrons on the plasma is increased. This improves spontaneous emission strength of the plasma. Spontaneous emission of the plasma is reflected by the reflecting mirror to the dichroic mirror after passing through the heating laser focusing lens group, and is received and analyzed by the spectrometer after being reflected by the dichroic mirror, obtaining content of chlorine ions.

In this embodiment, the first optical path system and the second optical path system are configured to perform excitation in a manner in which double beams are obliquely incident at an angle of 45°. The heating light source is wavelength-adjustable nanosecond laser.

In an optional implementation of this embodiment, the apparatus further includes a delay controller.

The delay controller that is separately connected to the femtosecond laser device, the heating light source, and the spectrometer, and is configured to: provide system time and separately control operation of the femtosecond laser device, the heating light source, and the spectrometer.

Figure 2:
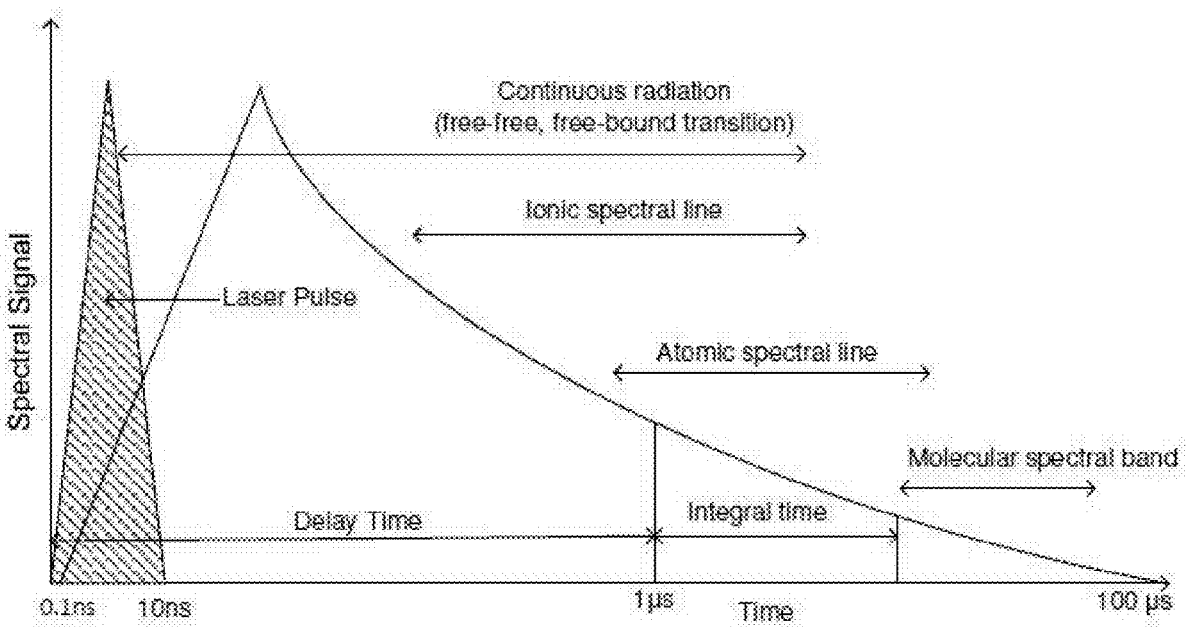
FIG. 2 is a schematic diagram of a spectral signal under different time according to Embodiment 1 of the present disclosure.

The delay controller is configured to provide system time. If laser is emitted at a moment 0, after the sample is broken down by ablative laser into the plasma (about 150 μs), after certain time, the plasma is expanded (about 1 nm at this time), and the plasma is heated by heating laser to increase a temperature, improving spectral line intensity and achieving objectives of improving sensitivity and reducing a detection limit. A plasma spectral line appears only after a period of time (about 10 ns). In this case, the spectrometer is configured to start receiving a signal, and a signal-to-noise ratio can be increased, as shown in FIG. 2.

A clustering algorithm is a data analysis algorithm in which clustering analysis is performed on spectral information obtained in a LIBS measurement process. Spectral intensities of different known elements such as calcium, aluminum, and sodium are measured. After spectral intensity distribution of these feature elements is obtained, components may be set according to correspondence between different elements and different spectral intensities. Sampling points with similar spectral intensities are set as a group. After parameters of the components are set, component information at the measurement and sampling point is determined to obtain a specific structure of the sampling point in a concrete sample.

A relational expression between the spectral intensity of chlorine ions and the content of chlorine ions is as follows:

$$I = FC_s A \frac{g_k e^{\frac{-E_k}{k_B T}}}{U(T)},$$

where

I is the spectral intensity of the chlorine ions, F is a system constant, $C_s$ is the content of the chlorine ions, A is a transition probability at a corresponding energy level, $g_k$ is energy level degeneracy, $E_k$ is energy at an energy level, $k_B$ is a Boltzmann constant, T is a plasma temperature, and U(T) is a partition function of the chlorine ions at the plasma temperature.

Similarly, other elements in the concrete sample also have similar spectral intensities. Therefore, content of corresponding elements can be obtained through the spectral intensities. Element content in different areas of the concrete sample is different. Therefore, specific information about the sampling point can be obtained through spectral information. For example, the content of each element is lower in an area with more pores, the carbon content near the aggregate (calcium carbonate) is higher, and the silicon and aluminum content near the cement colloid (calcium silicate) is higher.

For example, at a sampling point with a pore, overall sample mass is small. In this case, spectral line intensities of not only the chloride ions, but also the calcium, aluminum, sodium and other elements are also low. At a sampling point located near the aggregate, there is an obvious protrusion in a calcium spectral line, while spectral line intensities of other elements such as aluminum and sodium are low. By determining properties of different sampling points, a corresponding external standard model can be adopted to improve accuracy of a quantitative result and repeatability of a measurement result.

The optical path structure has the following advantages:

(1) The femtosecond laser device is used as an ablative light source. A pulse width of the ablative femtosecond laser is shorter. At a femtosecond level, the ablative femtosecond laser has shorter interaction time with a sample than general nanosecond laser. In a laser breakdown process, the plasma is formed about 150 picoseconds after the laser is contact with the sample, while interaction of the ablative femtosecond laser with the sample is ended before the formation of the plasma. This avoids energy loss due to shielding of laser energy by the plasma, and also avoids excessively strong bremsstrahlung as the plasma is heated. This method can improve utilization efficiency of laser energy, improve ablation efficiency, and increase a signal-to-noise ratio of chloride ion radiation.

Figure 3:
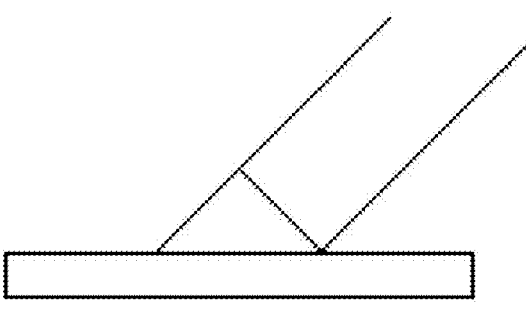
FIG. 3 is a schematic diagram of an incident angle of an optical path according to Embodiment 1 of the present disclosure.

(2) In the measurement process, excitation is performed in which the double beams are obliquely incident at an angle of 45°. That is, an included angle between an optical path of heating laser and an optical path of ablative laser, namely, an included angle between an optical path (1) and an optical path (2) in FIG. 1 is 45°. In this case, a radiation receiving area and an energy density of the plasma are more appropriate. As a power density is equal to laser energy/area. A larger area indicates that the spectrometer is more likely to receive a signal. However, increase of the area may lead to decrease of the power density. Therefore, the area and the power density need to be balanced. An incident angle of an optical path is as shown in FIG. 3.

(3) Wavelength-adjustable nanosecond laser is used as the heating light source to irradiate the plasma, such that a temperature of the plasma increases. A higher temperature of the plasma indicates stronger radiation strength. Different ions have different absorption peaks. A wavelength of the heating light source is controlled to selectively excite the chloride ions. This method can improve the spectral line intensity of chloride ions and increase the signal-to-noise ratio.

(4) A signal collection optical path adopts a common path structure. Radiation optical paths such as a heating optical path and a plasma optical path form the common path structure through same components and path. Through the common path structure, chromatic aberration in the system can be eliminated and a signal collection angle of the spectrometer can be increased, resolving a problem of a too small numerical aperture during optical fiber collection.

Figure 4:
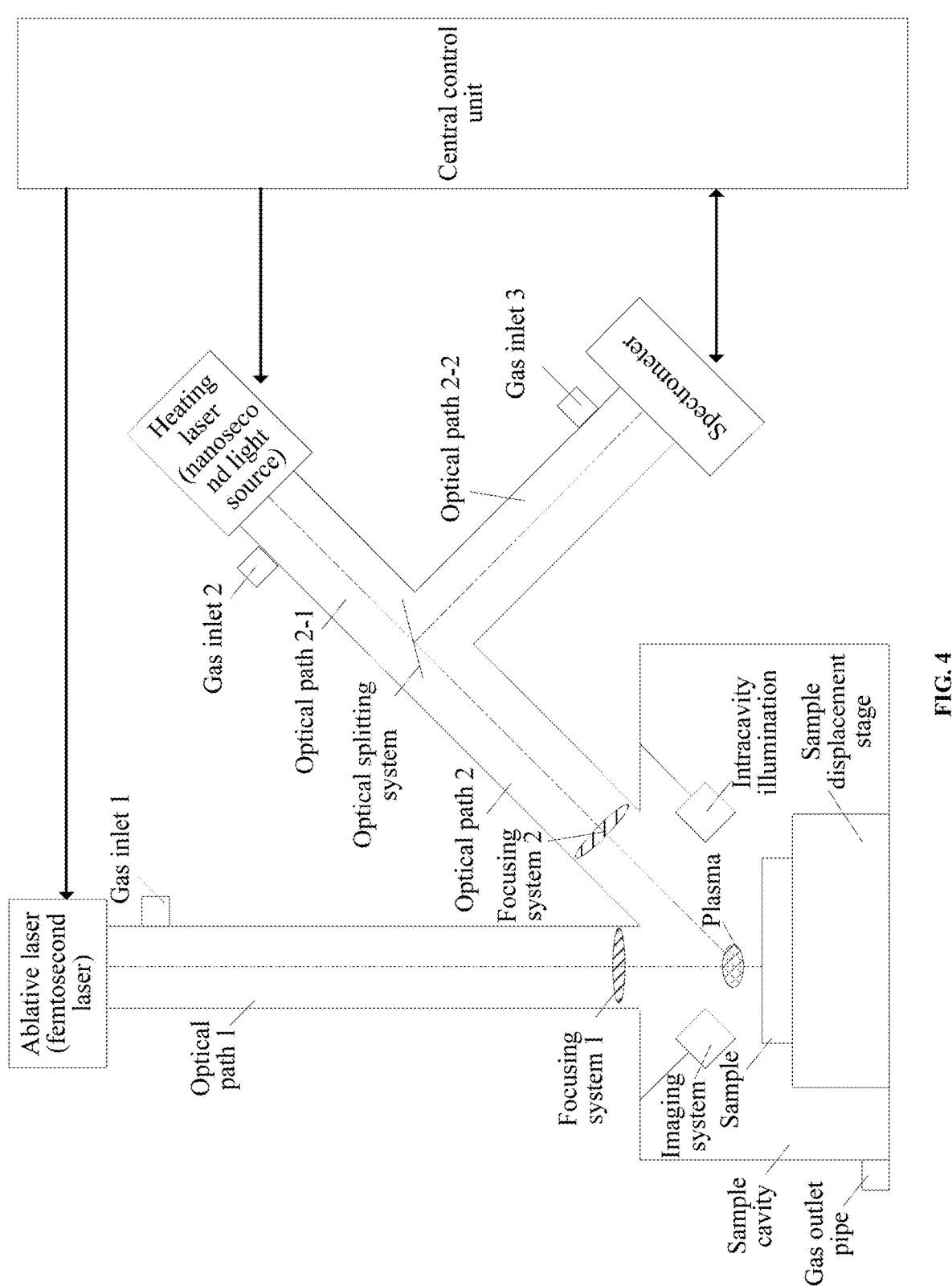
FIG. 4 is schematic diagram of a system structure according to Embodiment 1 of the present disclosure.
Figure 5:
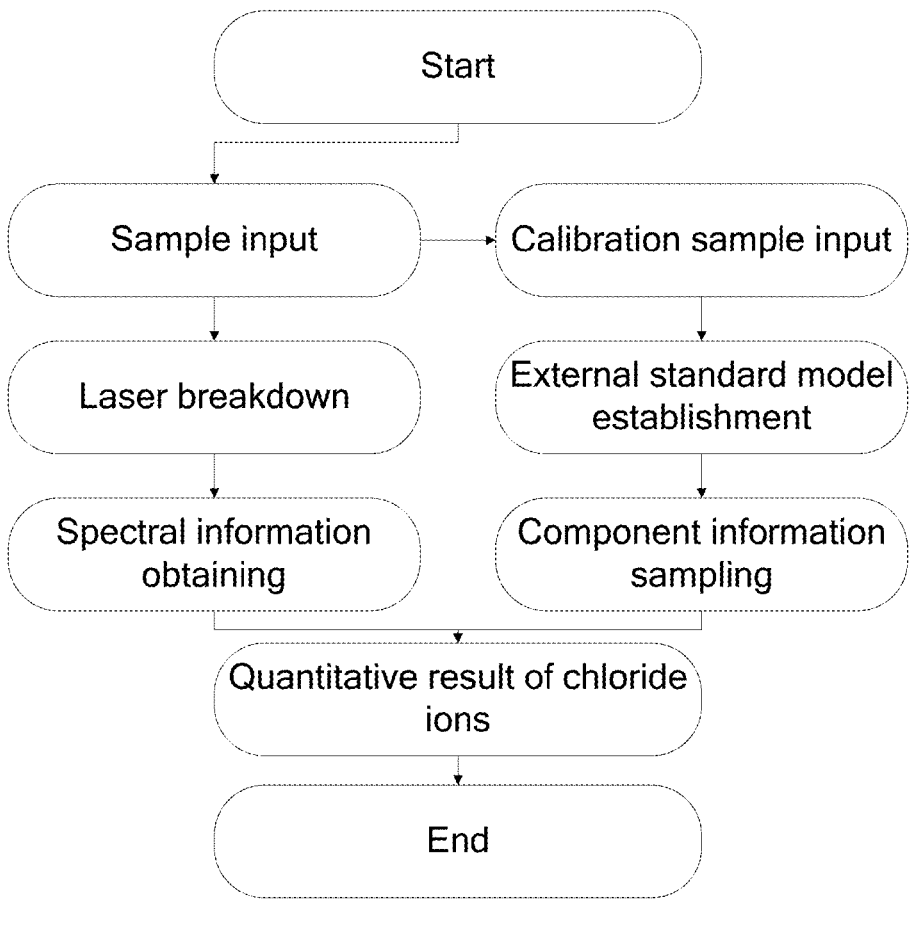
FIG. 5 is a flowchart of a measuring system according to Embodiment 1 of the present disclosure.

During specific application, as shown in FIG. 4 and FIG. 5, before content of chlorine ions of a to-be-tested sample is tested, a sample group with known content of chlorine ions is calibrated and measured to establish a composite calibration model of different components. Calibration curves are established according to different concrete components, sampling points, and the like. Calibration results are recorded in the central control unit. The central control unit is configured to divide the components according to the calibration results.

Laser of different intensities is absorbed differently by samples of different components, and therefore, an optimal laser intensity corresponding to the to-be-tested sample should first be confirmed, to improve radiation intensity of the plasma.

A relative position of the sample in a measurement system is controlled by a sample displacement stage through a transmission structure. In addition, the sample is illuminated by an intracavity illumination system, and the sampling point is located through an imaging system. Component information of the sampling point is estimated by the central control unit through the clustering algorithm. Laser parameter information corresponding to the component is separately sent by the central control unit according to a component information category to the femtosecond laser device and the heating light source. A modulation system of the laser device is configured to separately modulate the femtosecond laser device and the heating light source to an adaptive state. In addition, acquired information of the spectrometer is separately sent by the central control unit to a control system of the spectrometer.

First, femtosecond pulse is emitted by the femtosecond laser device, and the pulse is an ablative pulse. A moment at which the ablative pulse is emitted is an initial moment of a system clock. The ablative pulse is focused on a surface of a sample through a focusing system 1 along an optical path 1, such that energy is absorbed by the surface of the sample. Duration of the femtosecond laser varies according to the sampling point. Generally, system time is at about 10 fs when the ablative pulse ends. After the pulse ends, a plasma is formed at a system time of about 100 ps.

Then, the heating light source is configured to emit a heating pulse after a period of delay time according to parameters distributed by the central control unit. Emission time of the heating pulse changes according to the sampling point, and is generally about 10 ns of system time. The heating pulse is transmitted along an optical path 2-1 to pass through an optical splitting system, and is focused by a focusing system 2 along an optical path 2 to the plasma, to heat the plasma. The plasma is configured to continuously emit radiation during evolution. After energy of the heating laser is absorbed, a temperature of the plasma is increased, and radiation of the plasma is enhanced. The plasma radiation is reflected by the optical splitting system along the optical path 2 into an optical path 2-2, and reaches an acquisition window of the spectrometer.

Finally, according to the central control unit, a detector shutter is opened by the spectrometer after a period of delay time and the shutter is kept open for a period of time. During this period, a radiation signal is continuously acquired, and recorded in an acquisition system, and an acquired spectral signal is accumulated and output after the shutter is closed. A result of the spectral signal is fed back to the central control unit. Corresponding information is retrieved by the central control unit from an external calibration database according to the component information of the sampling point, the corresponding information is integrated with the result of the spectral signal, and a mass ratio of a chlorine element in a sample at the sampling point is finally output.

During the measurement, air pressure in a sample cavity and the optical path can be adjusted, and helium is simultaneously input from a gas inlet 1, a gas inlet 2, and a gas inlet 3, and the helium is output from a gas outlet pipe.

Embodiment 2

Figure 6:
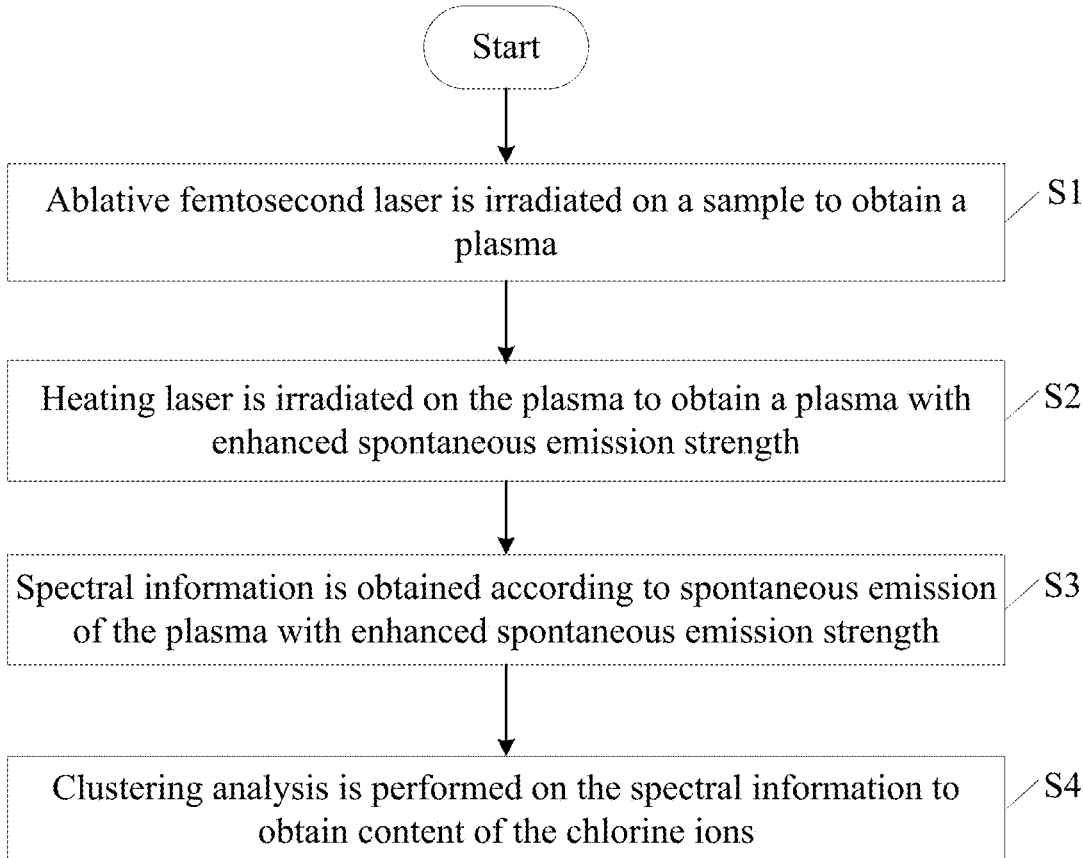
FIG. 6 is a flowchart of a method for measuring chlorine ions in concrete according to Embodiment 2 of the present disclosure.

As shown in FIG. 6, an embodiment provides a method for measuring chlorine ions in concrete based on the apparatus for measuring chlorine ions in concrete in Embodiment 1. The method includes the following steps.

In step S1, ablative femtosecond laser is irradiated on a sample to obtain a plasma.

In step S2, heating laser is irradiated on the plasma to obtain a plasma with enhanced spontaneous emission strength.

In step S3, spectral information is obtained according to spontaneous emission of the plasma with enhanced spontaneous emission strength.

In step S4, clustering analysis is performed on the spectral information to obtain content of the chlorine ions.

In an optional implementation of the this embodiment, the step S1 specifically includes the following steps.

In step S11, the ablative femtosecond laser emitted by a femtosecond laser device is focused by an ablative focusing lens group to obtain focused ablative femtosecond laser.

In step S12, the focused ablative femtosecond laser is vertically irradiated on a sample, to obtain a plasma.

In an optional implementation of the this embodiment, the step S2 specifically includes the following steps.

In step S21, the heating laser emitted by a heating light source is transmitted by a dichroic mirror to obtain transmitted heating laser.

In step S22, the transmitted heating laser is reflected by a reflecting mirror to obtain reflected heating laser.

In step S23, the reflected heating laser is focused by a heating laser focusing lens group to obtain focused heating laser.

In step S24, the heated laser is irradiated on the plasma at an incident angle of 45°, to obtain the plasma with enhanced spontaneous emission strength.

In an optional implementation of the this embodiment, the step S3 specifically includes the following steps.

In step S31, spontaneous emission of the plasma with enhanced spontaneous emission strength is focused by a heating laser focusing lens group to obtain focused plasma spontaneous emission.

In step S32, the focused plasma spontaneous emission is reflected by a reflecting mirror to obtain reflected plasma spontaneous emission.

In step S33, the reflected plasma spontaneous emission is reflected by a dichroic mirror for a second time to obtain plasma spontaneous emission that is reflected for a second time.

In step S34, the plasma spontaneous emission that is reflected for a second time is received by a spectrometer to obtain the spectral information.

In an optional implementation of the this embodiment, the step S4 specifically includes the following steps.

In step S41, the clustering analysis is performed on the spectral information to obtain a spectral intensity of the chlorine ions.

In step S42, the content of chlorine ions is determined according to a relational expression between the spectral intensity of chlorine ions and the chlorine ion content.

The relational expression between the spectral intensity of chlorine ions and the content of chlorine ions is as follows:

$$I = FC_s A \frac{g_k e^{\frac{-E_k}{k_B T}}}{U(T)},$$

where

I is the spectral intensity of the chlorine ions, F is a system constant, $C_s$ is the chlorine ion content, A is a transition probability at a corresponding energy level, $g_k$ is energy level degeneracy, $E_k$ is energy at an energy level, $k_B$ is a Boltzmann constant, T is a plasma temperature, and U(T) is a partition function of the chlorine ions at the plasma temperature.

The technical characteristics of the above embodiments can be employed in arbitrary combinations. To provide a concise description of these embodiments, all possible combinations of all the technical characteristics of the above embodiments may not be described; however, these combinations of the technical characteristics should be construed as falling within the scope defined by the specification as long as no contradiction occurs.

Specific examples are used herein to explain the principles and implementations of the present disclosure. The description of the examples is merely intended to help understand the method of the present disclosure and its core ideas. In addition, those of ordinary skill in the art can make various modifications to the specific implementations and application scope in accordance with the teachings of the present disclosure. In conclusion, the content of the description shall not be construed as limitations to the present disclosure.

What is claimed is:

1. An apparatus for measuring chlorine ions in concrete, the apparatus comprising:
   a first optical path system;
   a second optical path system,
   a spectrometer; and
   a central control unit,
   wherein the first optical path system comprises:
      a femtosecond laser device configured to emit ablative femtosecond laser;
      an ablative focusing lens group configured to focus the ablative femtosecond laser to obtain focused ablative femtosecond laser; and
      a sample configured to receive the focused ablative femtosecond laser to generate a plasma;
   the second optical path system comprises:
      a heating light source configured to emit heating laser, wherein the heating light source is wavelength-adjustable nanosecond laser;
      a dichroic mirror configured to transmit the heating laser to obtain transmitted heating laser;
      a reflecting mirror configured to reflect the transmitted heating laser to obtain reflected heating laser; and
      a heating laser focusing lens group configured to: focus the reflected heating laser to obtain focused heating laser, and irradiate the focused heating laser on the plasma to obtain a plasma with enhanced spontaneous emission strength,
   wherein the heating laser focusing lens group is further configured to focus spontaneous emission of the plasma with enhanced spontaneous emission strength to obtain focused plasma spontaneous emission, the reflecting mirror is further configured to reflect the focused plasma spontaneous emission to obtain reflected plasma spontaneous emission,
   the dichroic mirror is further configured to reflect the reflected plasma spontaneous emission for a second time to obtain plasma spontaneous emission that is reflected for a second time,
   the spectrometer is configured to receive the plasma spontaneous emission that is reflected for a second time to obtain spectral information, and
   the central control unit is configured to perform a clustering analysis on the spectral information to obtain content of the chlorine ions, and is specifically configured to: perform the clustering analysis on the spectral information to obtain a spectral intensity of the chlorine ions; and determine the content of the chlorine ions according to a relational expression between the spectral intensity of chlorine ions and the content of chlorine ions, wherein the relational expression between the spectral intensity of chlorine ions and the content of chlorine ions is follows:

$$I = FC_s A \frac{g_k e^{\frac{-E_k}{k_B T}}}{U(T)},$$

wherein

I is the spectral intensity of the chlorine ions, F is a system constant, $C_s$ is the content of the chlorine ions, A is a transition probability at a corresponding energy level, $g_k$ is energy level degeneracy, $E_k$ is energy at an energy level, $k_B$ is a Boltzmann constant, T is a plasma temperature, and U(T) is a partition function of the chlorine ions at the plasma temperature;

wherein the first optical path system and the second optical path system are configured to perform excitation in a manner in which double beams are obliquely incident at an angle of 45°, so as to balance an area and a power density; and before content of chlorine ions of a to-be-tested sample is tested, a sample group with known content of chlorine ions is calibrated and measured to establish a composite calibration model of different components; calibration curves are established according to the different components and sampling points; calibration results are recorded in the central control unit; and the central control unit divides the different components according to the calibration results.

2. The apparatus for measuring chlorine ions in concrete according to claim 1, further comprising:
   a delay controller that is separately connected to the femtosecond laser device, the heating light source, and the spectrometer, and is configured to: provide system time and separately control operation of the femtosecond laser device, the heating light source, and the spectrometer.

3. A method for measuring chlorine ions in concrete based on the apparatus for measuring chlorine ions in concrete according to claim 1, wherein the method comprises:
   irradiating ablative femtosecond laser on a sample to obtain a plasma;
   irradiating heating laser on the plasma to obtain a plasma with enhanced spontaneous emission strength;
   obtaining spectral information according to spontaneous emission of the plasma with enhanced spontaneous emission strength; and performing a clustering analysis on the spectral information to obtain content of the chlorine ions, specifically comprising:

performing the clustering analysis on the spectral information to obtain a spectral intensity of the chlorine ions; and determining the content of the chlorine ions according to a relational expression between the spectral intensity of the chlorine ions and the content of the chlorine ions;

wherein the relational expression between the spectral intensity of the chlorine ions and the content of the chlorine ions is follows:

$$I = FC_s A \frac{g_k e^{\frac{-E_k}{k_B T}}}{U(T)},$$

wherein

I is the spectral intensity of the chlorine ions, F is a system constant, $C_s$ is the content of the chlorine ions, A is a transition probability at a corresponding energy level, $g_k$ is energy level degeneracy, $E_k$ is energy at an energy level, $k_B$ is a Boltzmann constant, T is a plasma temperature, and U(T) is a partition function of the chlorine ions at the plasma temperature.

4. The method for measuring chlorine ions in concrete according to claim 3, wherein the irradiating ablative femtosecond laser on a sample to obtain a plasma specifically comprises:

focusing, by an ablative focusing lens group, the ablative femtosecond laser emitted by a femtosecond laser device to obtain focused ablative femtosecond laser; and vertically irradiating the focused ablative femtosecond laser on the sample, to obtain the plasma.

5. The method for measuring chlorine ions in concrete according to claim 3, wherein the irradiating heating laser on the plasma to obtain a plasma with enhanced spontaneous emission strength specifically comprises:

transmitting, by a dichroic mirror, the heating laser emitted by a heating light source to obtain transmitted heating laser;

reflecting, by a reflecting mirror, the transmitted heating laser to obtain reflected heating laser;

focusing, by a heating laser focusing lens group, the reflected heating laser to obtain focused heating laser; and irradiating the heated laser on the plasma at an incident angle of 45°, to obtain the plasma with enhanced spontaneous emission strength.

6. The method for measuring chlorine ions in concrete according to claim 3, wherein the obtaining spectral information according to spontaneous emission of the plasma with enhanced spontaneous emission strength specifically comprises:

focusing, by a heating laser focusing lens group, the spontaneous emission of the plasma with enhanced spontaneous emission strength to obtain focused plasma spontaneous emission;

reflecting, by a reflecting mirror, the focused plasma spontaneous emission to obtain reflected plasma spontaneous emission;

reflecting, by a dichroic mirror, the reflected plasma spontaneous emission for a second time to obtain plasma spontaneous emission that is reflected for a second time; and receiving, by a spectrometer, the plasma spontaneous emission that is reflected for a second time to obtain the spectral information.

7. The method for measuring chlorine ions in concrete according to claim 3, wherein the apparatus further comprises:

a delay controller that is separately connected to the femtosecond laser device, the heating light source, and the spectrometer, and is configured to: provide system time and separately control operation of the femtosecond laser device, the heating light source, and the spectrometer.

\* \* \* \* \*